(12) United States Patent
Dick et al.

(10) Patent No.: US 6,616,275 B1
(45) Date of Patent: Sep. 9, 2003

(54) METHOD AND DEVICE FOR COMPLETELY CORRECTING VISUAL DEFECTS OF THE HUMAN EYE

(75) Inventors: Manfred Dick, Gefell (DE); Joachim Fiedler, Crailsheim (DE); Eckhard Schroeder, Eckental (DE); Holger Maeusezahl, Jena (DE); Vasyl Molebny, Kiev (UA)

(73) Assignee: Asclepion Meditec GmbH, Jena (DE)

( * ) Notice: Subject to any disclaimer, the term of this patent is extended or adjusted under 35 U.S.C. 154(b) by 0 days.

(21) Appl. No.: 09/807,133

(22) PCT Filed: Aug. 11, 2000

(86) PCT No.: PCT/EP00/07822

§ 371 (c)(1),
(2), (4) Date: Jun. 28, 2001

(87) PCT Pub. No.: WO01/12114

PCT Pub. Date: Feb. 22, 2001

(30) Foreign Application Priority Data

Aug. 11, 1999  (DE) .......................................... 199 38 203
May 17, 2000  (DE) .......................................... 100 24 080

(51) Int. Cl.[7] .............................................. A61B 3/10
(52) U.S. Cl. ...................................................... 351/212
(58) Field of Search .................................. 351/205, 206, 351/211, 212, 246, 247; 623/6.31; 356/124

(56) References Cited

U.S. PATENT DOCUMENTS 5,777,719 A  7/1998  Williams et al. ............ 351/212
6,050,687 A  4/2000  Bille et al. ................... 351/212
6,271,914 B1 * 8/2001  Frey et al. .................... 356/124

FOREIGN PATENT DOCUMENTS

WO  9201417  2/1992
WO  9927334  6/1999

OTHER PUBLICATIONS

Klein, A. Stanley, "Optimal corneal ablation for eyes with arbitrary Hartmann–Shack aberrations", *J. Opt. Soc. Am.*, vol. 15, No. 9/Sep. 1998.

* cited by examiner

*Primary Examiner*—George Manuel
(74) *Attorney, Agent, or Firm*—Davidson, Davidson & Kappel, LLC

(57) ABSTRACT

The invention relates to a method and to a device for completely correcting visual defects of the human eye. The invention mentions combinations of measuring and treatment methods that allow the complete correction of defects of the human eye if applied according to the invention. Measuring methods are used that precisely detect the surface of the cornea and that also register the aberrations that occur in the beam path up to the retina. The computer-assisted evaluation of these measurement results combined with the calculation of optimally corrected lenses (for example after a cataract operation) or of optimally correcting cornea surfaces makes it possible to produce a patient-specific lens and/or to shape the retina so that it optimally corrects the aberration. To this end, the invention preferably uses a spot scanning excimer laser system and makes use of the topography of the eye.

2 Claims, 2 Drawing Sheets

METHOD AND DEVICE FOR COMPLETELY CORRECTING VISUAL DEFECTS OF THE HUMAN EYE

BACKGROUND OF THE INVENTION

Figure 1:
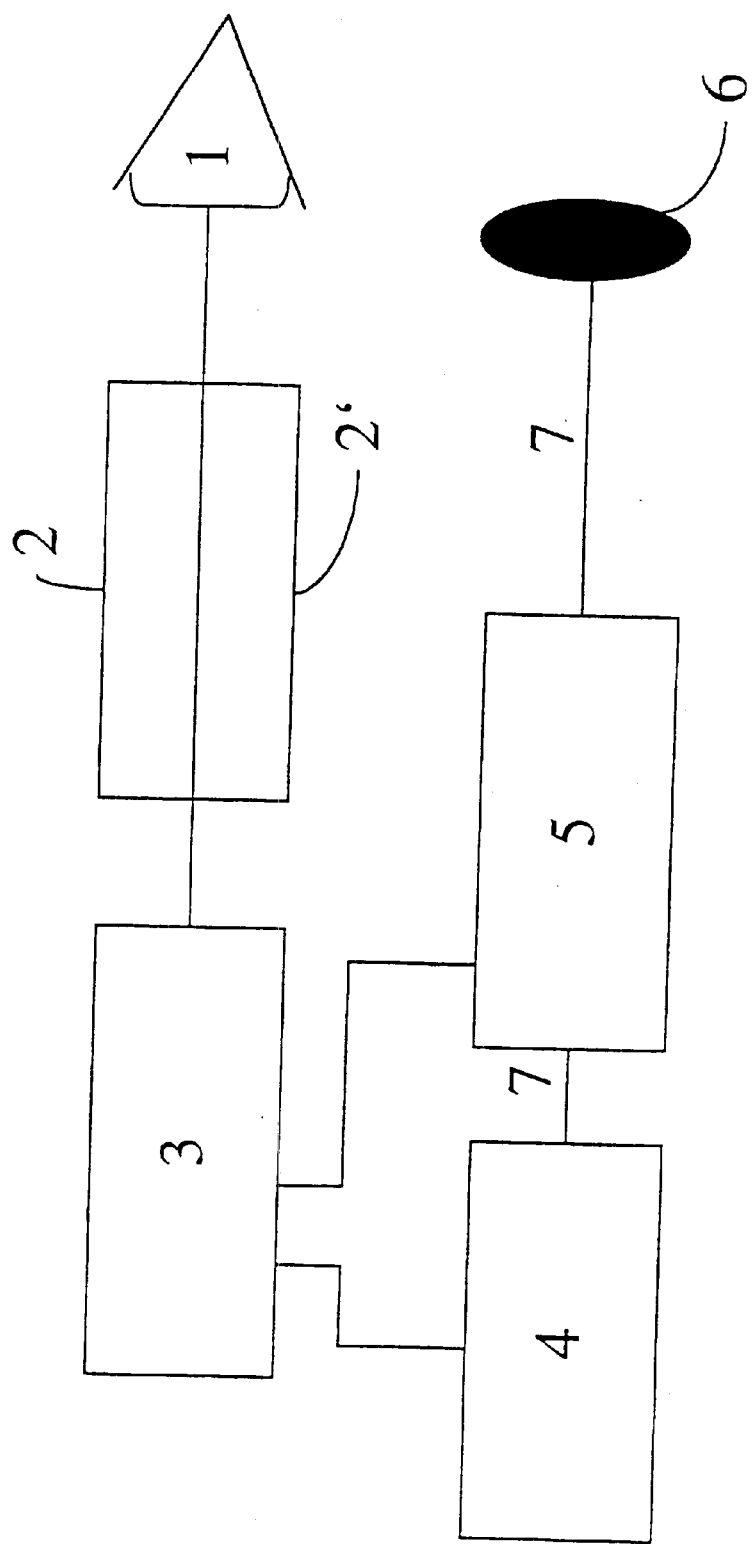

The present invention relates to a method and a device for correcting visual defects of the human eye.

In ophthalmology, it is known to shape the cornea by ablation of tissue in the case of amblyopia. In this context, the data on the aberration in the optical path of the eye is obtained by questioning the patient about his/her subjective impression of vision on the basis of corrections via standardized corrective lenses in front of the eye of the patient. Besides, methods exist for measuring the outer contour of the eye with the assistance of stripe- or ring-projection systems as are manufactured, for example, by the Orbtek, Tomey, or Technomed companies.

German Patent Application DE 197 05 119 A1 describes a method for improving a Shack-Hartmann sensor which can be used in the field of astronomy to measure wavefronts for surveying stars.

In German Patent 197 27 573 C1, a device and a method for shaping surfaces, in particular of lenses, by laser ablation of the surfaces is specified in a valuable contribution to the technological development.

It is felt to be a disadvantage of the related art that the correction of the lenses takes place only on the basis of suboptimum data on the causes of the visual defects such as irregularities of the cornea surface or aberration in the optical path. Consequently, only corrections according to the standard lens formulas of geometric optics are carried out.

SUMMARY OF THE INVENTION

Therefore, the object of the present invention is to provide a method and a device which permit complete correction of all refractive visual defects, including the aberrations of the optical path in the defective eye.

In particular, the objective is achieved by a device for correcting visual defects of an eye, including a coherent light source, a beam modification device for shaping and deflecting a beam of the coherent light source, provision being made for a wavefront analyzer device for analyzing a wavefront of the optical path in the eye. This device enables the data obtained from the analysis of the intraocular aberration to be taken into account in the correction of an existing optical system of an eye to be corrected. In this manner, the correction of the optical system of the eye is achievable with added precision.

The considered eye can be, in particular, a human eye but it is also conceivable to correct eyes of other living beings. Visual defects are, in particular, refractive visual defects such as myopia or hyperopia, irregularities of the cornea surface, or aberrations in the optical path.

Provided as coherent light source is preferably a laser, especially preferably a refractive laser, particularly preferably a spot scanning excimer laser. Conceivable is, moreover, a spot scanner using laser light in other ranges of the spectrum, such as a frequency-quintupled YAG laser, an IR laser of around 3 $\mu$m such as an Erbium:YAG laser emitting at 2.94 $\mu$m or a femtosecond laser (fs Laser).

The beam modification device is preferably composed of a device for shaping a beam and of a device for deflecting and aligning the beam. Preferably used as the device for shaping the beam are lens systems, diffractive structures, and refractive elements. Preferably used as the device for deflecting and aligning the beam are scanner arrangements, prisms, and mirrors.

Preferably usable as wavefront analyzer device is a Shack-Hartmann sensor, which is a sensor that is based on a method for analyzing wavefronts and is used, in particular in astronomy (see above). Using this wavefront analyzer device, it is possible to measure the whole wavefront emerging from the eye and, in this manner, to acquire data on the visual defects, including the intraocular aberration of the optical path also in the eye.

In a further exemplary embodiment of the present invention, provision is made for a device in which a topography analyzer unit for analyzing the surface of the eye is provided, as well. This analysis provides the data on the curvature and contour possessed by the eye surface, i.e., in particular by the cornea. In this manner, the complete data on the refractive visual defects of the eye is available to the system. Both the possibly not optimum surface contour of the eye, i.e., of the cornea, and the intraocular aberration can now be analyzed and are available to the system in the correction of the optical system of the eye. In this manner, it is possible to completely correct the visual defects of the eye and even to achieve a vision which exceeds that of the normal human eye. It is equally possible to correct aberrations only partly, thus producing a comprehensive correction only in combination with other vision aids. Preferably, it is also possible for aberrations to be generated purposely to make possible vision characteristics that are not or only rarely created by nature. These aberrations can then be selectively used for specific abilities (for example, spatial vision, accommodation, etc).

In a further exemplary embodiment of the present invention, provision is made for a device in which, moreover, a control unit for processing signals of the wavefront analyzer unit and/or for processing signals of the topography analyzer unit and/or for controlling the coherent light source and/or for controlling the beam modification device is provided. These control units permit evaluation of the data ascertained by the analyzer units. It is possible for the signals of the wavefront analyzer unit and the signals of the topography analyzer unit to be separately processed and evaluated in the control unit, or to process both data sets in one step. The control unit is preferably composed of several individual control units.

This data is preferably used for providing an ideal optical system. The parameters required for beam modification is determined from this data. These parameters can preferably be used in a further step for controlling the coherent light source, for example, to predetermine amplitude, pulse duration, and energy of the beam. Moreover, these parameters are also preferably used for controlling the beam modification device; here, to predetermine the target spot and the geometry of the beam in the target via the deflection of the beam.

Because of this, it is possible in a preferred exemplary embodiment to calculate, in particular, the shot positions for manufacturing the individual elements.

In a further preferred exemplary embodiment of the present invention, provision is made for a device in which the beam modification device is designed in such a manner that an intraocular lens and/or an eye lens and/or the cornea of the eye and/or a contact lens and/or an implantable contact lens (ICL) and/or a spectacle lens are processable via the beam. The beam, which is preferably controlled by the control unit, now enables an element or workpiece of the lens system to be processed in such a manner that the visual defects or aberration are completely corrected. Such an element is preferably an intraocular lens (IOL) which is prefabricated prior to a corresponding operation. This is particularly preferably an ICL (implantable contact lens) which is placed onto the lens. Based on the entire available data on the visual defects, including the aberration of the eye, this IOL or ICL can be shaped in such a manner that it corrects all existing visual defects. It is also conceivable for the correction to be carried out on the eye lens itself with the assistance of the beam which is preferably controlled by the control unit.

Moreover, it is conceivable to carry out a correction by processing the cornea. It is also preferred to manufacture contact lenses which, in a patient-specific manner, correct all individual defects going beyond the refractive eye defect, such as aberrations, unsymmetrical cylinders, and irregularities of the cornea. Besides, it is also possible to manufacture individual spectacle lenses. Besides excimer spot processing, methods of the optical industry, such as the single point diamond turning method, can also be used for this purpose. In this manner, all elements of the affected optical system can be used for correcting the eye defects.

It is also possible to use a combination of the individual (partly) corrected elements. This is an advantage, in particular if the theoretically possible correction via one element would result in excessive stressing of this element, and if such stressing appears not to be advisable, in particular from the medical point of view.

Moreover, the objective is achieved by a method according to the present invention for correcting visual defects of an eye, the optical path of the eye being determined via a wavefront analysis, and an ideal lens system being calculated which would result in a correction of the visual defects of the eye. This method is particularly preferably employed using a device according to the present invention. In this method, the intraocular aberration of the optical path is available for calculating the correction of the optical system for conversion into an ideal optical system.

In a further method according to the present invention, it is particularly preferred to analyze the topography of the eye as well. In this method, consequently, additional data on the defective vision of the eye is available, in particular on aberrations, unsymmetrical cylinders, and irregularities of the cornea.

In another preferred method, the ideal optical system is provided on the basis of the data obtained from the wavefront analysis and/or from the topography analysis. For this, it is particular preferred to provide only one element from this optical system. In this manner, the correcting element or the correcting elements is/are manufactured in a further step on the basis of the complete data of the defective vision. This procedure thus leads to the complete correction of the defective vision.

In a further preferred method, shot positions for manufacturing the ideal optical system are calculated using the data obtained from the wavefront analysis and/or from the topography analysis. In this manner, it is advantageously possible to use the laser spot excimer method for manufacturing the individual elements of the optical systems. The shot positions are optimized depending on the materials to be used and considering the time needed for manufacture.

In another method of the present invention, the old optical system of the eye is reshaped into the calculated ideal optical system. To this end, either elements of the old optical system are processed directly or correspondingly corrected elements are manufactured and inserted or old elements are replaced with new elements. This method allows the old (defective) optical system of the eye to be converted into a (new) ideal optical system. It is especially preferred to manufacture a new lens or an ICL according to the spot scanning principle using an excimer laser.

The optical system preferably includes, as elements, the eye lens and/or an intraocular lens and/or the cornea of the eye and/or a contact lens and/or an ICL and/or at least one spectacle lens. Via refractive surgery, it is possible, for example, for the cornea of the eye to be reshaped so as to correct the existing defective vision (for example, the surface of the cornea via photorefractive keratectomy, PRK, or by ablation of inner tissue layers of the cornea using laser assisted in situ keratomileusis, LASIK). These elements not only feature rotationally geometric corrections but individual structures for correcting the defective vision of the patients. In this manner, it is possible to manufacture intraocular lenses or contact lenses, in particular ICLs which, once they are brought into the lens system, not only roughly correct the defective vision of the eye as in known methods heretofore but which additionally correct all irregularities, unsymmetries, and beam distortions, as well. In this manner, it is possible to attain a vision which exceeds that of the normal human eye. Besides, this method makes it possible to manufacture spectacle lenses which likewise correct all irregularities, unsymmetries, and beam distortions of the defective eye or of the old optical system, as well.

In a particularly preferred method of the present invention, individual optical elements, in particular lenses, of the ideal optical system are manufactured in a first step for testing the ideal optical system and, in a second step, these individual elements are removed and other elements, in particular the cornea, are reshaped correspondingly. This method makes possible an increase in acceptance since the determined previously shot positions can now be applied to an optical element, such as a lens, and this (planned) correction immediately conveys the impression of how the completely corrected eye would see later. The viewer is now able to subjectively test the effect of a correspondingly corrected optical system, and to assess the corrected vision performance or even a super-vision even before an operation of the cornea. In a second step, this lens can be removed from the ideal optical system, and the cornea then be ideally shaped to provide the correspondingly corrected vision. The provisional optical element is preferably a lens which can then be inserted into the optical system on a spectacle frame for the viewer. The material to which the shot pattern is preliminarily applied is particularly preferably a wet contact lens.

In this context, it is particularly advantageous for the contact lens to be selected such that the spherocylindrical aberrations of the patient to be treated are already corrected by this lens. Then, only the previously measured higher aberrations are to be corrected on this contact lens using the treatment laser. It is particularly advantageous for the soft contact lens to have a refractive power and ablation characteristic which substantially correspond to the cornea. Because of this, the shot positions of the provisional optical element will later correspond to the own optical element, in particular to the cornea. The provisional optical element, in particular the contact lens, is centrically aligned and reference axes of the wavefront measurement as well as the axis of the eye coincide. It is preferred to use materials such as PMMA as the ablation material of the provisional optical element. In this context, in particular also when comparing this material to the cornea, the different refractive indices of the two media are also allowed for in addition to the differing ablation depth. Being constant factors, these can be mathematically determined and transformed very well.

This method, via the data, makes it possible to shoot a provisional lens which produces the same wavefront correction as a possibly intended later reshaping of the cornea. To this end, a lens is preferably made available on a stand so that no contact of this lens with the eye is required. It is particularly preferred for the manufacture of the (provisional) lens to be carried out during the measurement of the wavefront in the optical system. In doing so, the provisional lens is preferably iteratively processed and then, the wavefront is remeasured again until no aberration of the overall system can be detected anymore. In such a procedure, it is particularly preferable for the eye of the patient to be fixed in position, for example, by a graticule. It is also conceivable to bring the distance of the provisional lens from the cornea to zero and to work with a contact lens on the eye, the contact lens then being particularly preferably processed in an iterative manner while it rests on the eye. Preferably, processing is interrupted for carrying out a vision test subsequent to performing corresponding partial processing steps. In this manner, the best vision can be iteratively approached with the direct assistance of the patient and using the excimer laser. It is particularly preferred to improve the aberrations of different order separately: 1. astigmatism, 2. coma, 3. . . .

For this purpose, it is especially preferred to manufacture spectacles having an outer and an inner spherical surface, patterns being additionally applied to at least one of these surfaces, the transfer function of the pattern being phase-conjugated with the irregular distortions of the wavefront which are caused by the optical system or the eye. Because of this, it is possible for these specially determined corrections to be carried out by such spectacles.

For manufacturing such spectacles in a preferred embodiment, the average values of the emmetropia and of the wavefront of the eye are determined, the radii of the outer and inner surfaces are calculated which represent a correction of these average values of the emmetropia, at least one of the surfaces is manufactured with radii of curvature which have been changed on the order of the maximum deviation of the wavefront from the emmetropia, which have been corrected by the previous step, and then this deviation of the surface is used according to the pattern of the irregular distortions of the wavefront of the optical system or of the eye.

In a further preferred method, these irregularities of the surface are applied to the surface either by material removal or material deposition. This removal can be carried out by laser irradiation, thermal or a thermal processes, for example, by ablation.

The deposition onto the surface can be carried out in a layerwise manner.

It is particularly preferred for the surfaces in the different sectors to be exactly adapted to the eye so that, for example, two regions can be formed in which the compensation can be selected as a function of the accommodation state of the eye if it uses the corresponding region.

It is particularly preferable for the surfaces to be changed in such a manner that the geometrical displacement of the plane of the spectacles from the basic plane of the optical system of the eye is also compensated for.

Moreover, the objective is achieved by an ideal optical system which is manufactured according to a method according to the present invention and/or using a devices according to the present invention, the optical system including elements made of materials which are suitable for implantation and/or for adhesion and/or for ablation, in particular plastic or glass. By selecting these materials of the lens system according to the present invention, compatibility in using these elements is guaranteed. Such materials are, for example, PMMA, acrylic, silicone, or a combination of these materials.

In a further exemplary embodiment of the present invention, provision is made for an ideal optical system including elements which contain refractive and/or diffractive structures. In known methods heretofore, refractive and/or diffractive structures are only used in beam shaping. A minilens system guides and shapes the entering beam to attain a special beam distribution in the target plane. The use of such refractive and/or diffractive structures on individual elements of an optical system allows visual defects to be selectively corrected in an exceptionally ideal manner. Using these structures, it is thus possible to correct individual, non-steady aberrations but also to give the optical systems characteristics which a normal human eye does not possess.

The objective of the present invention is achieved, moreover, by an element of an (ideal) lens system having refractive and/diffractive structures. Such elements can include intraocular lenses, modified cornea, contact lenses, ICLs, or spectacle lenses.

Figure 2:
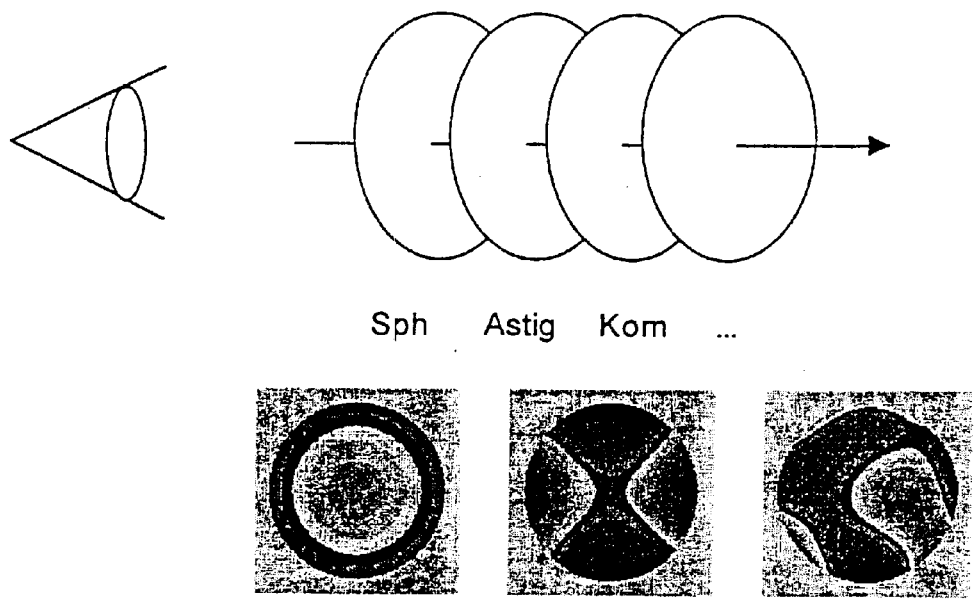
Figure 2:
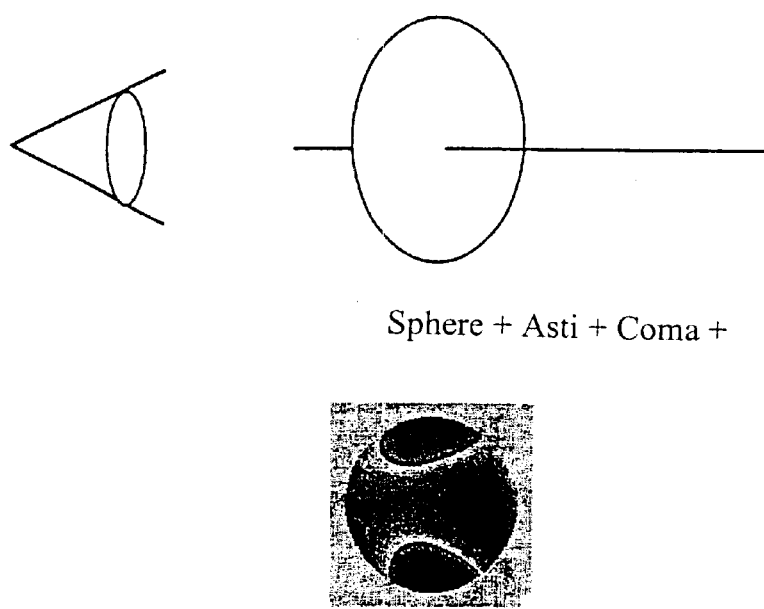

In the following, exemplary embodiments of the present invention and advantageous refinements will be explained in greater detail on the basis of drawings. In this context, FIG. 1 shows a block diagram for an exemplary embodiment of a device according to the present invention for correcting an aberration in the optical path of an eye;

FIG. 2 shows a schematic representation of an arrangement for separately measuring visual defects (FIG. 2a) and an arrangement involving superposition of all defects (FIG. 2b).

DETAILED DESCRIPTION

FIG. 1 depicts a block diagram for an exemplary embodiment of a device according to the present invention for correcting visual defects of an eye. A wavefront analyzer unit 2 and a topography analyzer unit 2' are connected to a control unit 3. Control unit 3 is connected to a laser 4 and to a beam modification device 5 via a bus. A lens 6 is depicted downstream of beam modification device 5. An eye 1 is shown upstream of wavefront analyzer unit 2 and topography analyzer In the operating state, the beams of wavefront analyzer unit 2 and topography analyzer unit 2' scan eye 1 and transmit the obtained signals to control unit 3. In control unit 3, the signals are processed and the ideal optical system for this eye 1 is calculated. In the depicted case, an ideal lens 6 is calculated here as element of the optical system. In control unit 3, in particular, all shot positions needed for laser 4 to manufacture ideal lens 6 are calculated on the basis of the data obtained from the signals, taking into account the laser-relevant data. Subsequently, control unit 3 triggers laser 4, determining energy and pulse rate of beam 7. Beam 7 is guided through beam modification device 5. In beam modification device 5, beam 7 is shaped and deflected via scanners and lens systems according to the calculated shot positions via the input of control unit 3, so that customer-specific lens 6 is made by ablation of material on the raw lens via controlled laser beam 7. Preferably, control unit 3 can also be designed in several partial control units which can be connected to individual components of the device.

In this manner, a new and advantageous method and a device for completely correcting visual defects of the human eye have been specified. Combinations of measuring and processing methods have been specified which, when used according to the present invention, enable the human eye to be completely corrected. In doing so, measuring methods are used which can precisely measure the surface of the cornea and which also record the aberrations arising in the further optical path up to the retina. The computer-aided evaluation of these measuring results, in conjunction with the calculation of ideally corrected eye lenses (for example, after cataract operations) or of ideally correcting cornea surfaces, makes it possible to manufacture a patient specific lens and/or to shape the cornea in an ideally correcting manner, preferably using a spot scanning excimer laser in a topography-aided manner.

In particular, the correction can be effected via the modification of an element of the optical system. Thus, for improving the vision of a patient having a cataract and a defective vision, it is sufficient to completely correct the intraocular lens. In such a case, it is no longer necessary to carry out a refractive operation in addition to the cataract operation.

FIG. 2 shows a schematic representation of an arrangement for separately measuring visual defects (FIG. 2a) and an arrangement involving superposition of all defects (FIG. 2b). In this connection, the same optical system is shown, including the eye and the four optical elements. Using these optical elements, it is now possible to correct individual visual defects by using the individual optical elements specifically for correcting individual visual defects. Thus, for example, the first optical element can be used for correcting a spherical aberration, the second optical element can be used to compensate for an astigmatism, and the third optical element allows a coma to be compensated for. To this end, it is possible for the individual optical elements to be processed one after the other using the shot positions determined by the correction parameters, and to be reshaped individually. Preferably, a vision test is carried out subsequent to each (partial) correction to be able to subjectively test the change.

FIG. 2b, on the other hand, shows the effect that a superposition of all defects on one optical element would have, and how the above-indicated compensation would have to be transferred or finally is transferred to the optical element in the lower case. In fact, subsequent to predetermining the individual corrections of the individual optical elements, these corrections can be transferred to a provisional optical element. The shot positions underlying this correction can then be transferred, for example, to the cornea in a further step; the provisional optical element can then be dispensed with.

In this manner, a device and a method for correcting visual defects of the human eye have been provided which elegantly permit correction of all refractive visual defects, including the aberrations of the optical path in the defective eye, it also being possible for the individual defects to be corrected in advance by iterative correction, preferably on one or several provisional optical elements, and to be assessed by the viewer without surgery of the eye having taken place yet.

What is claimed is:

1. A method for correcting visual defects of an eye comprising:

determining an optical path of the eye via a wavefront analysis;

calculating an ideal optical system which would result in a correction of the visual defects of the eye;

manufacturing individual provisional elements of the ideal optical system;

testing the ideal optical system using the individual provisional elements; and replacing the individual provisional elements with other correspondingly reshaped elements.

2. The method as recited in claim 1 wherein the individual provisional elements are lenses and the other correspondingly reshaped elements include a correspondingly reshaped cornea.

* * * * *